US010173948B2

(12) United States Patent
Im et al.

(10) Patent No.: US 10,173,948 B2
(45) Date of Patent: Jan. 8, 2019

(54) METHOD FOR OLIGOMERIZATION OF OLEFINS

(71) Applicant: LG CHEM, LTD., Seoul (KR)

(72) Inventors: Seul Ki Im, Daejeon (KR); Yong Ho Lee, Daejeon (KR); Eun Ji Shin, Daejeon (KR); Ki Soo Lee, Daejeon (KR); Jin Young Park, Daejeon (KR); Seok Pil Sa, Daejeon (KR); Yoon Ki Hong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 15/738,068

(22) PCT Filed: Aug. 16, 2016

(86) PCT No.: PCT/KR2016/008980
§ 371 (c)(1),
(2) Date: Dec. 19, 2017

(87) PCT Pub. No.: WO2017/047936
PCT Pub. Date: Mar. 23, 2017

(65) Prior Publication Data
US 2018/0155254 A1 Jun. 7, 2018

(30) Foreign Application Priority Data

Sep. 15, 2015 (KR) .................. 10-2015-0130577

(51) Int. Cl.
*C07C 2/32* (2006.01)
*C08F 2/34* (2006.01)
*C08F 4/69* (2006.01)
*C08F 10/00* (2006.01)
*B01J 31/14* (2006.01)
*B01J 31/18* (2006.01)

(52) U.S. Cl.
CPC ............... *C07C 2/32* (2013.01); *B01J 31/143* (2013.01); *B01J 31/188* (2013.01); *C08F 2/34* (2013.01); *C08F 4/69* (2013.01); *C08F 10/00* (2013.01); *B01J 2231/20* (2013.01); *B01J 2531/62* (2013.01); *C07C 2531/14* (2013.01); *C07C 2531/22* (2013.01)

(58) Field of Classification Search
CPC .. B01J 2231/20; B01J 2531/62; B01J 31/143; B01J 31/188; C07C 2531/14; C07C 2531/22; C07C 2/32; C07C 2/36; C07C 11/02; C07C 11/107; C07C 2531/24; C07C 2531/34; C07C 211/54; C07C 2531/12; C07C 2531/18; C07C 2531/30; C07C 2/34
See application file for complete search history.

(56) References Cited

U.S. PATENT DOCUMENTS

| 7,012,121 | B2 | 3/2006 | Carnahan et al. |
| 9,266,983 | B2 | 2/2016 | Li et al. |
| 9,394,213 | B2 | 7/2016 | Shiraki et al. |
| 9,421,533 | B2 | 8/2016 | Wang et al. |
| 9,637,508 | B2 | 5/2017 | Lee et al. |
| 2008/0058486 | A1 | 3/2008 | McCullough et al. |
| 2012/0172645 | A1* | 7/2012 | Sydora .................. B01J 31/143 585/511 |
| 2015/0225492 | A1 | 8/2015 | Gao et al. |

FOREIGN PATENT DOCUMENTS

| CN | 1651142 A | 8/2005 |
| JP | 2004306014 A | 11/2004 |
| JP | 2013515601 A | 5/2013 |
| JP | 2013133467 A | 7/2013 |
| KR | 1020010110790 A | 12/2001 |
| KR | 1020140124732 A | 10/2014 |
| KR | 1020150058049 A | 5/2015 |
| WO | 2014094114 A1 | 6/2014 |
| WO | 2014181247 A1 | 11/2014 |

OTHER PUBLICATIONS

Tao Wang, et al., Mixed aluminoxanes: efficient cocatalysts for bisphosphineamine/Cr(III) catalyzed ethylene tetramerization toward 1-octene, Applied Petrochemical Research, Mar. 13, 2015, 5, 2, 143-149.
Amir Jabri, et al., Isolation of a Cationic Chromium(II) Species in a Catalytic System for Ethylene Tri- and Tetramerization, Organometallics, 2006, 25(3) 715-718.

* cited by examiner

*Primary Examiner* — Sharon Pregler
(74) *Attorney, Agent, or Firm* — Dentons US LLP

(57) ABSTRACT

The present disclosure relates to a method for oligomerization of olefins. The method for oligomerization of olefins according to the present disclosure not only provides excellent catalytic activity and stable process operation, but also exhibits high selectivity to 1-hexene or 1-octene by using a catalyst system including an activity modifier.

8 Claims, 1 Drawing Sheet

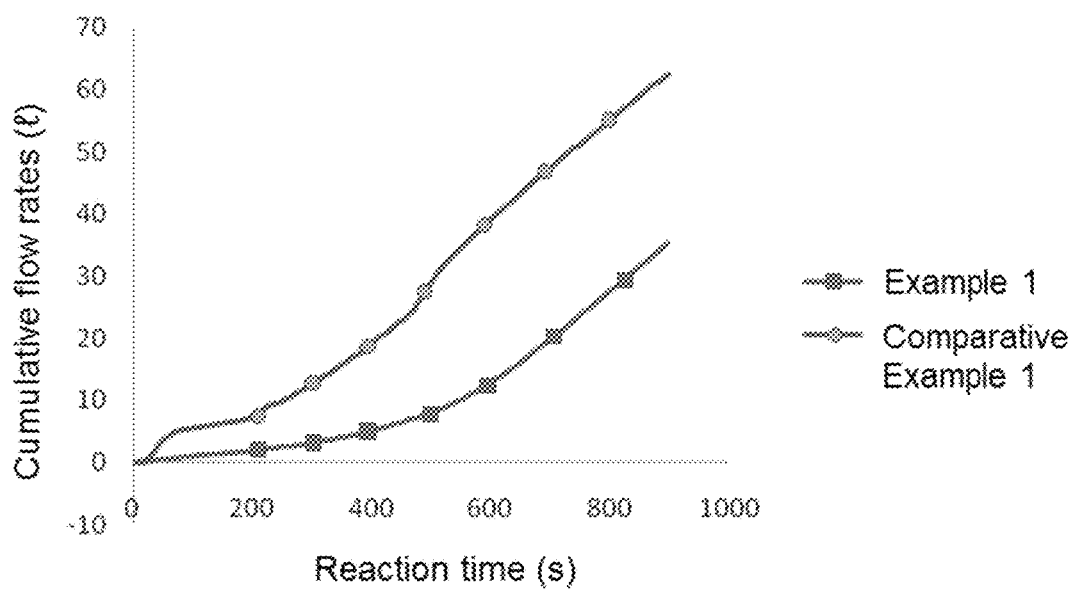

METHOD FOR OLIGOMERIZATION OF OLEFINS

CROSS REFERENCE TO RELATED APPLICATION

This application is a National Stage Application of International Application No. PCT/KR2016/008980, filed Aug. 16, 2016, and claims the benefit of Korean Patent Application No. 10-2015-0130577, filed Sep. 15, 2015, contents of which are incorporated herein by reference in their entirety for all purposes as if fully set forth below.

The present disclosure relates to a method for oligomerization of olefins, and more particularly relates to a method for oligomerization of olefins with improved efficiency by controlling activity of oligomerization of the olefins.

BACKGROUND OF ART

Technical Field

Linear alpha-olefins such as 1-hexene, 1-octene, and the like are used in a cleaner, a lubricant, a plasticizer, and so on, and particularly, are widely used as a comonomer for adjusting the density of a polymer during the preparation of linear low density polyethylene (LLDPE).

Such linear alpha-olefins have been mostly prepared through a Shell higher olefin process. However, since the method synthesizes alpha-olefins of various lengths together according to Schultz-Flory distribution, there is an inconvenience of needing an additional separation process in order to obtain a specific alpha-olefin.

In order to resolve this problem, a method of selectively synthesizing 1-hexene through a trimerization reaction of ethylene and a method of selectively synthesizing 1-octene through tetramerization of ethylene have been suggested. Further, various studies on catalysts enabling such selective oligomerization of ethylene have been undertaken.

However, the catalyst systems for the oligomerization of olefins proposed so far tend to make it difficult to operate a stable process, such as a rapid increase in the reaction rate due to a high initial activity of the reaction.

Accordingly, there is a need to develop a method for oligomerization of olefins that not only exhibits high selectivity to linear alpha-olefins, but also enables stable process operation.

DETAILED DESCRIPTION OF THE INVENTION

Technical Problem

The present disclosure provides a method for oligomerization of olefins that not only exhibits high selectivity to 1-hexene or 1-octene, but also enables excellent catalytic activity and stable process operation.

Technical Solution

According to the present disclosure,
a method for oligomerization of olefins is provided, including the steps of:
preparing a catalyst composition including a ligand including at least one diphosphino aminyl moiety, a chromium source, and a cocatalyst represented by the following Chemical Formula 1;
preparing a catalyst system by mixing the catalyst composition with an activity modifier represented by the following Chemical Formula 2; and contacting olefinic monomers with the catalyst system.

[Chemical Formula 1]

In Chemical Formula 1,
$R^{11}$, $R^{12}$, and $R^{13}$ are the same as or different from each other, and are independently hydrogen, a halogen, a $C_1$-$C_{20}$ hydrocarbyl group, or a $C_1$-$C_{20}$ hydrocarbyl group substituted with a halogen, and
a is an integer of 2 or more.

[Chemical Formula 2]

In Chemical Formula 2,
D is aluminum or boron, and
each $R^{21}$ is the same as or different from each other, and are independently a $C_1$-$C_{20}$ hydrocarbyl group, or a $C_1$-$C_{20}$ hydrocarbyl group substituted with a halogen.

Hereinafter, the method for oligomerization of olefins will be explained in detail.

Prior to this, technical terms in the present specification are only for mentioning specific embodiments, and they are not intended to restrict the present invention unless there is a particular mention about them.

Singular expressions used herein may include plural expressions unless they are differently expressed contextually.

The meaning of the term "include" used in the specification embodies specific characteristics, areas, essences, steps, actions, elements, and/or components, and does not exclude existence or addition of other specific characteristics, areas, essences, steps, actions, elements, components, and/or groups.

In general, the catalyst system for oligomerization of olefins has a problem that it makes it difficult to operate a stable process, such as a rapid increase in the reaction rate due to a high initial activity of the reaction. Adjusting the reaction conditions at the beginning of the reaction to stabilize the process may adversely affect the oligomerization of olefins, such as reduced activity of the catalyst system or lowered selectivity to linear alpha-olefins throughout the reaction.

However, as a result of continuous research of the present inventors, it is recognized that if a catalyst system in which a specific activity modifier is added to a catalyst composition including a ligand, a chromium source, and an alkylaluminoxane as a cocatalyst is used for oligomerization of olefins, it not only exhibits high selectivity to 1-hexene or 1-octene, but also enables excellent catalytic activity and stable process operation.

According to an embodiment of the disclosure,
a method for oligomerization of olefins is provided, including the steps of:
preparing a catalyst composition including a ligand including at least one diphosphino aminyl moiety, a chromium source, and a cocatalyst represented by the following Chemical Formula 1;
preparing a catalyst system by mixing the catalyst composition with an activity modifier represented by the following Chemical Formula 2; and
contacting olefinic monomers with the catalyst system.

[Chemical Formula 1]

In Chemical Formula 1, $R^{11}$, $R^{12}$, and $R^{13}$ are the same as or different from each other, and are independently hydrogen, a halogen, a $C_1$-$C_{20}$ hydrocarbyl group, or a $C_1$-$C_{20}$ hydrocarbyl group substituted with a halogen, and a is an integer of 2 or more.

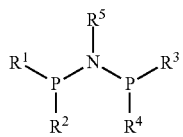

[Chemical Formula 2]

In Chemical Formula 2,

D is aluminum or boron, and each $R^{21}$ is the same as or different from each other, and are independently a $C_1$-$C_{20}$ hydrocarbyl group, or a $C_1$-$C_{20}$ hydrocarbyl group substituted with a halogen.

According to an embodiment of the present disclosure, the method for oligomerization of olefins uses a catalyst system treated with an activity modifier represented by Chemical Formula 2. The rate of increase in the initial catalytic activity of the catalyst system may be lowered due to the action of the activity modifier, and the catalytic activity may be restored after a lapse of time.

Furthermore, if the activity modifier is applied when the reaction is actively carried out and the reaction rate is difficult to control, as well as in the initial stage or at the beginning of the reaction, it is possible to control the activity. Therefore, the activity modifier plays a role of temporarily delaying the increase of the catalytic activity, and it enables a stable process operation without hindering inherent catalytic activity and selectivity of the catalyst system.

In particular, in the method for oligomerization of olefins, the above-explained action and effect may be manifested depending on the time of addition of the activity modifier or the presence of the cocatalyst.

According to an embodiment of the disclosure, the above-explained action and effect due to the activity modifier may be manifested by preparing the catalyst composition by mixing the ligand, the chromium source, and the cocatalyst, mixing the activity modifier with the catalyst composition, and initiating the oligomerization reaction of olefins.

That is, the above-described action and effect may be obtained by injecting the activity modifier at any time in the beginning or middle of the reaction after the formation of the catalyst composition. Alternatively, the above-described action and effect may not be expected if the activity modifier is mixed with the ligand, the chromium source, and the cocatalyst simultaneously, and introduced into the reactor, or if the activity modifier is mixed with a catalyst solution not including the cocatalyst.

According to the embodiment of the present disclosure, a step of preparing a catalyst composition including a ligand including at least one diphosphino aminyl moiety, a chromium source, and a cocatalyst represented by the following Chemical Formula 1 is carried out.

As the ligand included in the catalyst composition, conventional ligands used for oligomerization of olefins may be applied without particular limitations. Preferably, the ligand including at least one diphosphino aminyl moiety may be advantageous for the high selectivity to 1-hexene and 1-octene.

Specifically, the ligand may be a compound represented by the following Chemical Formula 3 or Chemical Formula 4.

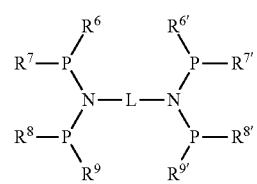

[Chemical Formula 3]

In Chemical Formula 3, each of $R^1$ to $R^5$ is independently a $C_1$-$C_{10}$ alkyl group, a $C_1$-$C_{10}$ alkenyl group, a $C_4$-$C_{10}$ cycloalkyl group, a $C_1$-$C_{10}$ alkoxy group, a $C_6$-$C_{15}$ aryl group, a $C_7$-$C_{20}$ alkylaryl group, or a $C_7$-$C_{20}$ arylalkyl group.

[Chemical Formula 4]

$$\begin{array}{c} R^7-P \diagup \stackrel{R^6}{\phantom{P}} \quad \stackrel{R^{6'}}{\phantom{P}} \diagdown P-R^{7'} \\ N-L-N \\ R^8-P \diagdown \stackrel{}{\phantom{P}} \quad \stackrel{}{\phantom{P}} \diagup P-R^{8'} \\ R^9 \quad R^{9'} \end{array}$$

In Chemical Formula 4,

L is a linker connecting between the diphosphino aminyl moieties by 2 to 8 carbon atoms, and each of $R^6$ to $R^9$ and $R^{6'}$ to $R^{9'}$ is independently a $C_1$-$C_{10}$ alkyl group, a $C_1$-$C_{10}$ alkenyl group, a $C_4$-$C_{10}$ cycloalkyl group, a $C_1$-$C_{10}$ alkoxy group, a $C_6$-$C_{15}$ aryl group, a $C_7$-$C_{20}$ alkylaryl group, or a $C_7$-$C_{20}$ arylalkyl group.

Herein, at least one hydrogen contained in the alkyl, alkenyl, cycloalkyl, alkoxy, aryl, alkylaryl, and arylalkyl may be substituted with a $C_1$-$C_{10}$ alkyl group, a $C_1$-$C_{10}$ alkoxy group, a halogen, or cyano group.

Preferably, $R^1$ to $R^4$ of Chemical Formula 3, and $R^6$ to $R^9$ and $R^{6'}$ to $R^{9'}$ of Chemical Formula 4, are independently methyl, ethyl, propyl, propenyl, propynyl, butyl, cyclohexyl, 2-methylcyclohexyl, 2-ethylcyclohexyl, 2-isopropylcyclohexyl, benzyl, phenyl, tolyl, xylyl, o-methylphenyl, o-ethylphenyl, o-isopropylphenyl, o-t-butylphenyl, o-methoxyphenyl, o-isopropoxyphenyl, m-methylphenyl, m-ethylphenyl, m-isopropylphenyl, m-t-butylphenyl, m-methoxyphenyl, m-isopropoxyphenyl, p-methylphenyl, p-ethylphenyl, p-isopropyl phenyl, p-t-butylphenyl, p-methoxyphenyl, p-isopropoxyphenyl, 2,6-dimethylphenyl, 2-ethyl-6-methylphenyl, cumyl, mesityl, biphenyl, naphthyl, anthracenyl, methoxy, ethoxy, phenoxy, tolyloxy, dimethylamino, thiomethyl, or trimethylsilyl.

The L of Chemical Formula 4 is a linker connecting between the diphosphino aminyl moieties by 2 to 8 carbon atoms. Preferably, the linker may have a structure in which one or more groups selected from the group consisting of a $C_1$-$C_{10}$ aliphatic group, a substituted or unsubstituted $C_4$-$C_{10}$ alicyclic group, and a substituted or unsubstituted $C_6$-$C_{15}$ aromatic group are bonded.

Specifically, the linker may be a group wherein one or more of a $C_1$-$C_{20}$, $C_1$-$C_{10}$, or $C_1$-$C_5$ linear or branched alkylene group or alkenylene group (for example, one or two alkylene groups or alkenylene groups) is bonded with one or more of a $C_6$-$C_{20}$ or $C_6$-$C_{10}$ arylene group (for example, one or two arylene groups). Herein, the $C_6$-$C_{20}$ arylene group may be substituted or unsubstituted with a $C_1$-$C_5$ alkyl group.

Further, at least one end of the linker may be substituted or unsubstituted with a $C_6$-$C_{20}$ or $C_6$-$C_{10}$ aryl group.

Particularly, if the linker consists of a $C_5$-$C_{20}$ aliphatic group, at least one end thereof is substituted with a $C_6$-$C_{20}$ aryl group, and such an aryl group may be unsubstituted or additionally substituted with a $C_1$-$C_5$ alkyl group.

Meanwhile, the chromium source in the catalyst composition is a compound complexed to the nitrogen atom of the diphosphino aminyl moiety included in the ligand.

The chromium source may be an organic or inorganic chromium compound with an oxidation state of chromium of 0 to 6, for example, a chromium metal, or a compound wherein any organic or inorganic radical is bonded to chromium. Herein, the organic radical may be an alkyl, an alkoxy, an ester, a ketone, an amido radical, and the like, which have 1 to 20 carbon atoms per radical, and the inorganic radical may be a halide, sulfate, oxide, and the like.

Preferably, the chromium source is a compound that may exhibit high activity for oligomerization of olefins and may be easily used and acquired, and may be one or more compounds selected from the group consisting of chromium(III) acetylacetonate, chromium(III) chloride tetrahydrofuran, chromium(III) 2-ethylhexanoate, chromium(III) acetate, chromium(III) butyrate, chromium(III) pentanoate, chromium(III) laurate, and chromium(III) stearate.

Further, the cocatalyst in the catalyst composition is an organometallic compound capable of activating the complex compound of the above-explained ligand and the chromium source, and preferably may be a compound represented by the following Chemical Formula 1.

   [Chemical Formula 1]

In Chemical Formula 1,
$R^{11}$, $R^{12}$, and $R^{13}$ are the same as or different from each other, and are independently hydrogen, a halogen, a $C_1$-$C_{20}$ hydrocarbyl group, or a $C_1$-$C_{20}$ hydrocarbyl group substituted with a halogen, and
a is an integer of 2 or more.

Specifically, the cocatalyst may be one or more compounds selected from the group consisting of methyl aluminoxane, ethyl aluminoxane, butyl aluminoxane, and isobutyl aluminoxane.

In particular, modified methylaluminoxane (MMAO), which is a compound wherein some of the methyl groups in the methyl aluminoxane are substituted with another alkyl group, may be used for the cocatalyst. For example, the modified methylaluminoxane may be a compound wherein 40 mol % or less, or 5 mol % to 35 mol % of the methyl groups in the methyl aluminoxane is substituted with a straight-chain or branched alkyl group having 3 to 10 carbon atoms. Examples of commercially available modified methylaluminoxane include MMAO-12, MMAO-3A, and MMAO-7.

The content ratio of the components composing the catalyst composition may be determined by considering the catalytic activity and the selectivity to linear alpha-olefins.

According to an embodiment of the disclosure, it is preferable for the catalytic activity and the selectivity in the catalyst composition that a mole ratio of the ligand to the chromium in the chromium source to the aluminum in the cocatalyst is controlled to be 1:1:1 to 10:1:10,000, or 1:1:100 to 5:1:3000.

The components composing the catalyst composition may be mixed at the same time or in an arbitrary order in the presence of an appropriate solvent. The appropriate solvent may be heptane, toluene, cyclohexane, methylcyclohexane, 1-hexene, 1-octene, diethylether, tetrahydrofuran, acetonitrile, dichloromethane, chloroform, chlorobenzene, methanol, acetone, and so on.

According to an embodiment of the disclosure, a step of preparing a catalyst system by mixing the catalyst composition with an activity modifier represented by the following Chemical Formula 2 is carried out.

   [Chemical Formula 2]

In Chemical Formula 2,
D is aluminum or boron, and
each $R^{21}$ is the same as or different from each other, and are independently a $C_1$-$C_{20}$ hydrocarbyl group, or a $C_1$-$C_{20}$ hydrocarbyl group substituted with a halogen.

As described above, the activity modifier plays a role of delaying the increase of catalytic activity, and it enables stable process operation without hindering inherent catalytic activity and selectivity of the catalyst system. In particular, the above-described action and effect may be exhibited by injecting the activity modifier at the initiation of the reaction after the formation of the catalyst composition.

Specifically, the activity modifier may be one or more compounds selected from the group consisting of trimethylaluminum, triethylaluminum, triisopropylaluminum, triisobutylaluminum, diethylaluminum chloride, and ethylaluminum dichloride.

In particular, when the modified methylaluminoxane is used for the cocatalyst, using triethylaluminum as the activity modifier is preferable to control the activity.

The activity modifier may be added within a range that does not inhibit the inherent catalytic activity and selectivity of the catalyst system.

According to an embodiment of the disclosure, it is preferable for delaying the rise of the initial catalytic activity of the reaction and restoring the catalytic activity again in the catalyst system that a mole ratio of the chromium in the chromium source to the D in the activity modifier is controlled to be 1:10 to 1:3000, or 1:100 to 1:1200.

According to an embodiment of the disclosure, a step of contacting olefinic monomers with the catalyst system is carried out.

The above-explained step is carrying out the oligomerization reaction of olefinic monomers in the presence of the catalyst system, and may be carried out by using devices and technologies known to be applicable to the oligomerization of olefins.

For example, the oligomerization reaction of olefins may be carried out by a homogeneous liquid phase reaction in the presence or absence of an inert solvent, by a slurry reaction using a catalyst system that is partially or not totally dissolved, by a bulk reaction in which the alpha-olefin, which is the product, acts as a main medium, or by a gas phase reaction.

In the oligomerization reaction of olefins, gaseous ethylene may be used as the olefinic monomer.

The oligomerization reaction of olefins may be carried out in the presence of an inert solvent such as benzene, toluene, xylene, cumene, heptane, cyclohexane, methylcyclohexane, methylcyclopentane, n-hexane, 1-hexene, 1-octene, and so on.

The oligomerization reaction of olefins may be carried out at a temperature of about 0 to 200° C., about 0 to 150° C., about 30 to 100° C., or about 50 to 100° C. Furthermore, the reaction may be carried out at a pressure of about 1 to 300 bar, or about 2 to 150 bar.

Advantageous Effects

The method for oligomerization of olefins not only exhibits high selectivity to 1-hexene or 1-octene, but also enables excellent catalytic activity and stable process operation.

BRIEF DESCRIPTION OF DRAWINGS

FIG. 1 is a graph showing cumulative flow rates of products over reaction time in the oligomerization reaction of olefins according to an example and a comparative example of the present disclosure.

DETAILED DESCRIPTION OF THE EMBODIMENTS

Hereinafter, preferable examples and comparative examples are presented for better understanding of the present invention. However, the following examples are only for illustrating the present invention and the present invention is not limited to or by them.

Synthesis Example

All the reactions were progressed under argon using Schlenk techniques or a glovebox. The synthesized ligands were analyzed by $^1$H (500 MHz) and $^{31}$P (202 MHz) NMR spectra using a Varian 500 MHz spectrometer. Under the argon atmosphere, 10 mmol of 2-ethyl-6-methylaniline and 3 equiv. to amine of triethylamine were dissolved in 80 mL of dichloromethane in a flask. While the flask was immersed in a water bath, 20 mmol of chlorodiphenylphosphine was slowly added thereto, and the mixture was stirred overnight. The solvent was removed under vacuum, and then tetrahydrofuran was added thereto, followed by sufficient stirring, and triethylammonium chloride salt was removed using an air-free glass filter. The solvent was removed from the filtrate to obtain a product (a ligand compound of the following Chemical Formula a).

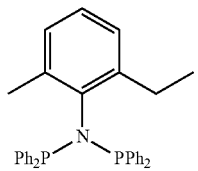

[Chemical Formula a]

Example 1

Under the argon gas atmosphere, chromium(III) acetylacetonate (17.5 mg, 0.05 mmol) and the ligand compound according to the synthesis example (1.1 eq. to Cr) were added to a flask, 100 mL of methylcyclohexane was added thereto, and the mixture was stirred to prepare a ligand solution of 0.5 mM (based on Cr).

After a Parr reactor with a capacity of 600 ml was placed under vacuum at 180° C. for 2 h, the interior of the reactor was substituted with argon, and the temperature was decreased to 60° C. Thereafter, 140 g of methylcyclohexane and 0.25 ml (Al/Cr=600) of modified methylaluminoxane (MMAO, 8.6 wt % isoheptane solution) were introduced, and 1.5 ml of the above 0.5 mM ligand solution (0.75 μmol) was introduced thereto and stirred.

After 1.5 ml of a 0.05 M triethylaluminum solution was introduced thereto and stirred, an ethylene line valve was opened to fill the interior of the reactor with ethylene, and the mixture was stirred at 1000 rpm for 15 min at the temperature of 60° C.

The ethylene line valve was closed, the reactor was cooled down to 0° C. using a dry ice/acetone bath, non-reacted ethylene was slowly vented, and 1 ml of nonane (GC internal standard) was introduced. The liquid part of the reactor was slightly recovered and quenched with water, and the organic layer was filtered with a PTFE syringe filter to perform GC analysis.

400 mL of an ethanol/HCl solution (10 vol % of an aqueous 12 M HCl solution) was introduced to the remaining reaction solution, and the mixture was stirred and filtered to obtain a polymer. The obtained polymer was dried in a vacuum oven at 60° C. overnight and weighed.

Comparative Example 1

The oligomerization of olefins was conducted according to the same method as in Example 1, except that the triethylaluminum solution was not introduced thereto.

Comparative Example 2

The oligomerization of olefins was conducted according to the same method as in Example 1, except that 4.5 ml of 0.1 M triethylaluminum solution (in methylcyclohexane) (Al/Cr=600) was introduced instead of the modified methylaluminoxane (MMAO), and the 1.5 ml of a 0.05 M triethylaluminum solution was not introduced thereto.

TABLE 1

|  |  | Example 1 | Comparative Example 1 | Comparative Example 2 |
|---|---|---|---|---|
| Reaction time (min) |  | 15 | 15 | 15 |
| Duration of the catalytic activity (min) |  | 7.7 | 12.3 | — |
| Catalytic activity (ton/mol Cr/h) | total | 310 | 461 | — |
|  | conversion value | 604 | 562 | — |
| Alpha-olefin in liquid (wt %) | 1-$C_6$ | 26.4 | 40.5 | — |
|  | 1-$C_8$ | 62.3 | 50.2 | — |
|  | Sum | 88.7 | 90.7 | — |
| Solid (wt %) |  | 0.7 | 0.4 | — |

In the above Table 1, the duration of the catalytic activity is defined as the time from an x-intercept where the section in which a flow rate of ethylene is constant after start of the oligomerization reaction of ethylene is extended by a trend line to a point that the oligomerization reaction is completed (that is, 15 min after the start of the reaction).

Further in Table 1, the conversion value of the catalytic activity is a value of which the catalytic activity value shown in the oligomerization reaction of ethylene is weighted based on the duration of the catalytic activity.

A graph showing the cumulative flow rates of the products over reaction time of Example 1 and Comparative Example 1 is shown in FIG. 1.

Referring to Table 1 and FIG. 1, in Example 1, compared to Comparative Example 1, it was possible to operate a stable process, because the increase of the catalytic activity was delayed at the initial stage of the reaction. The activity of Example 1 was also comparable to that of Comparative Example 1 after the lapse of time. Referring to FIG. 1, it was confirmed that the slope (T=0.076x−33.25) of the later part of the reaction in the graph of Example 1 closely coincided with the slope (T=0.081x−9.67900) in Comparative Example 1.

In Comparative Example 2, triethylaluminum was introduced instead of the modified methylaluminoxane (MMAO), but the oligomerization reaction did not proceed. That is, it was confirmed that triethylaluminum did not function as a cocatalyst. Also, it was confirmed that when triethylaluminum was mixed with a catalyst solution in which no cocatalyst was present, the action of the activity modifier could not be manifested.

The invention claimed is:

1. A method for oligomerization of olefins comprising the steps of:
    preparing a catalyst composition comprising a ligand comprising at least one diphosphino aminyl moiety, a chromium source, and a cocatalyst represented by the following Chemical Formula 1;
    after preparing the catalyst composition, preparing a catalyst system by mixing the catalyst composition with an activity modifier which is one or more compounds selected from the group consisting of trimethylaluminum, triethylaluminum, triisopropylaluminum, triisobutylaluminum, diethylaluminum chloride, and ethylaluminum dichloride; and
    contacting olefinic monomers with the catalyst system:

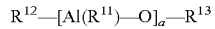 [Chemical Formula 1]

in Chemical Formula 1,
$R^{11}$, $R^{12}$, and $R^{13}$ are the same as or different from each other, and are independently hydrogen, a halogen, a $C_1$-$C_{20}$ hydrocarbyl group, or a $C_1$-$C_{20}$ hydrocarbyl group substituted with a halogen, and
a is an integer of 2 or more.

2. The method for oligomerization of olefins according to claim 1, wherein the cocatalyst is one or more compounds selected from the group consisting of methyl aluminoxane, ethyl aluminoxane, butyl aluminoxane, and isobutyl aluminoxane.

3. The method for oligomerization of olefins according to claim 1, wherein the chromium source is one or more compounds selected from the group consisting of chromium (III) acetylacetonate, chromium(III) chloride tetrahydrofuran, chromium(III) 2-ethylhexanoate, chromium(III) acetate, chromium(III) butyrate, chromium(III) pentanoate, chromium(III) laurate, and chromium(III) stearate.

4. The method for oligomerization of olefins according to claim 1, wherein the ligand is a compound represented by the following Chemical Formula 3 or Chemical Formula 4:

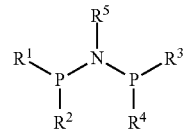 [Chemical Formula 3]

in Chemical Formula 3,
each of $R^1$ to $R^5$ is independently a $C_1$-$C_{10}$ alkyl group, a $C_1$-$C_{10}$ alkenyl group, a $C_4$-$C_{10}$ cycloalkyl group, a $C_1$-$C_{10}$ alkoxy group, a $C_6$-$C_{15}$ aryl group, a $C_7$-$C_{20}$ alkylaryl group, or a $C_7$-$C_{20}$ arylalkyl group;

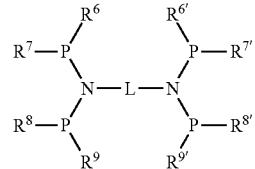 [Chemical Formula 4]

in Chemical Formula 4,
L is a linker connecting between the diphosphino aminyl moieties by 2 to 8 carbon atoms, and
each of $R^6$ to $R^9$ and $R^{6'}$ to $R^{9'}$ is independently a $C_1$-$C_{10}$ alkyl group, a $C_1$-$C_{10}$ alkenyl group, a $C_4$-$C_{10}$ cycloalkyl group, a $C_1$-$C_{10}$ alkoxy group, a $C_6$-$C_{15}$ aryl group, a $C_7$-$C_{20}$ alkylaryl group, or a $C_7$-$C_{20}$ arylalkyl group.

5. The method for oligomerization of olefins according to claim 1, wherein in the catalyst composition, a mole ratio of the ligand to the chromium in the chromium source to the aluminum in the cocatalyst is 1:1:1 to 10:1:10,000.

6. The method for oligomerization of olefins according to claim 1, wherein in the catalyst system, a mole ratio of the chromium in the chromium source to the D in the activity modifier is 1:10 to 1:3000.

7. The method for oligomerization of olefins according to claim 1, wherein the olefinic monomers comprise gaseous ethylene.

8. The method for oligomerization of olefins according to claim 1, wherein the step of contacting the olefinic monomers with the catalyst system is carried out at a temperature of 0 to 200° C., and at a pressure of 1 to 300 bar.

* * * * *